(12) United States Patent
Aklog et al.

(10) Patent No.: US 12,220,568 B2
(45) Date of Patent: Feb. 11, 2025

(54) SYSTEMS AND METHODS FOR PRIMING A FLUID LINE

(71) Applicant: PAVmed, Inc., New York, NY (US)

(72) Inventors: Lishan Aklog, Purchase, NY (US); Richard Yazbeck, Norwell, MA (US); Jessie Gifford, Sharon, MA (US); Julian Fricks, La Jolla, CA (US); Peter Aliski, New York, NY (US)

(73) Assignee: PAVmed Inc., New York, NY (US)

(*) Notice: Subject to any disclaimer, the term of this patent is extended or adjusted under 35 U.S.C. 154(b) by 0 days.

(21) Appl. No.: 18/275,878

(22) PCT Filed: Feb. 4, 2022

(86) PCT No.: PCT/US2022/015332
§ 371 (c)(1),
(2) Date: Aug. 4, 2023

(87) PCT Pub. No.: WO2022/170110
PCT Pub. Date: Aug. 11, 2022

(65) Prior Publication Data
US 2024/0091464 A1  Mar. 21, 2024

Related U.S. Application Data

(60) Provisional application No. 63/145,824, filed on Feb. 4, 2021.

(51) Int. Cl.
*A61M 5/36* (2006.01)
*A61M 5/168* (2006.01)
(Continued)

(52) U.S. Cl.
CPC .......... *A61M 5/36* (2013.01); *A61M 5/16804* (2013.01); *F15D 1/025* (2013.01); *A61M 2005/1402* (2013.01); *A61M 5/16877* (2013.01)

(58) Field of Classification Search
CPC ............ A61M 5/36; A61M 2005/1402; A61M 39/10; A61M 39/24; A61M 2039/242; A61M 2039/2486
See application file for complete search history.

(56) References Cited

U.S. PATENT DOCUMENTS

| 780,986 A | 1/1905 | Francis |
|---|---|---|
| 1,724,881 A | 8/1929 | Lund |

(Continued)

FOREIGN PATENT DOCUMENTS

| DE | 2452117 A1 | 5/1976 |
|---|---|---|
| EP | 0228514 B1 | 8/2018 |

(Continued)

*Primary Examiner* — Laura A Bouchelle

(57) ABSTRACT

Systems and methods for exhausting air from a flow pathway are provided. The systems can include a flow resistor having an input coupled to a fluid source and an outlet to output a fluid at an output flow rate, the flow resistor including an adjustable flow channel for modifying the output flow rate of the fluid flowing through the flow resistor; and a priming device having an elongated portion, the elongated portion being substantially rigid axially and configured for insertion through the outlet of the flow resistor to engage the flow resistor and adjust the output flow rate to allow air to be exhausted from the flow pathway through the flow resistor.

19 Claims, 11 Drawing Sheets

(51) Int. Cl.
*F15D 1/02* (2006.01)
*A61M 5/14* (2006.01)

(56) References Cited

U.S. PATENT DOCUMENTS

| | | | |
|---|---|---|---|
| 2,647,531 | A | 8/1953 | Berck |
| 2,781,061 | A | 2/1957 | Frey |
| 2,802,486 | A | 8/1957 | Frey |
| 3,837,362 | A | 9/1974 | Barnes |
| 4,011,894 | A | 3/1977 | Barnes |
| 4,361,147 | A | 11/1982 | Aslanian et al. |
| 4,383,550 | A | 5/1983 | Sotokazu |
| 4,572,004 | A | 2/1986 | White |
| 4,573,994 | A | 3/1986 | Fischell et al. |
| 5,100,389 | A | 3/1992 | Vaillancourt |
| 5,190,075 | A | 3/1993 | Tentler et al. |
| 5,800,405 | A | 9/1998 | McPhee |
| 6,053,888 | A | 4/2000 | Kong |
| 6,213,986 | B1 | 4/2001 | Darling et al. |
| 7,022,107 | B1 | 4/2006 | Christensen et al. |
| 7,255,680 | B1 | 8/2007 | Gharib |
| 7,654,982 | B2 | 2/2010 | Carlisle et al. |
| 8,622,976 | B2 | 1/2014 | Aklog et al. |
| 8,758,307 | B2 * | 6/2014 | Grimm .......... A61M 5/385 604/247 |
| 8,869,826 | B2 | 10/2014 | Chappel et al. |
| 9,155,834 | B2 | 10/2015 | Aklog et al. |
| 9,435,450 | B2 | 9/2016 | Meunnich |
| 10,596,314 | B2 | 3/2020 | Lee |
| 2002/0156464 | A1 | 10/2002 | Blischak et al. |
| 2003/0040709 | A1 | 2/2003 | Mason |
| 2004/0221854 | A1 | 11/2004 | Hete et al. |
| 2005/0034766 | A1 | 2/2005 | Rado |
| 2005/0159708 | A1 | 7/2005 | Sidler |
| 2006/0004330 | A1 | 1/2006 | Carlisle et al. |
| 2007/0000488 | A1 | 1/2007 | Koemer et al. |
| 2007/0066939 | A1 | 3/2007 | Krulevitch et al. |
| 2007/0088267 | A1 | 4/2007 | Shekalim |
| 2008/0154240 | A1 | 6/2008 | Shippert |
| 2009/0088724 | A1 | 4/2009 | Chebator et al. |
| 2011/0125103 | A1 | 5/2011 | Rondeau |
| 2011/0226354 | A1 | 9/2011 | Thoradson |
| 2012/0048403 | A1 | 3/2012 | Chappel et al. |
| 2014/0083529 | A1 | 3/2014 | Aklog et al. |
| 2014/0096552 | A1 | 4/2014 | Foesel et al. |
| 2019/0167914 | A1 | 6/2019 | Staley et al. |
| 2020/0324102 | A1 * | 10/2020 | Fangrow .......... A61M 39/22 |
| 2020/0325999 | A1 | 10/2020 | Aklog et al. |

FOREIGN PATENT DOCUMENTS

| | | |
|---|---|---|
| EP | 2722500 B1 | 8/2018 |
| EP | 3711792 A1 | 9/2020 |
| FR | 1437915 A | 5/1966 |
| FR | 2148395 A2 | 3/1973 |
| GB | 2014277 A | 8/1979 |
| GB | 1554629 A | 10/1979 |
| JP | S61164564 A | 7/1986 |
| WO | 81/00519 A1 | 3/1981 |
| WO | 2019/009898 A1 | 1/2019 |
| WO | 2022169800 A1 | 8/2022 |
| WO | 2022170110 A1 | 8/2022 |

\* cited by examiner

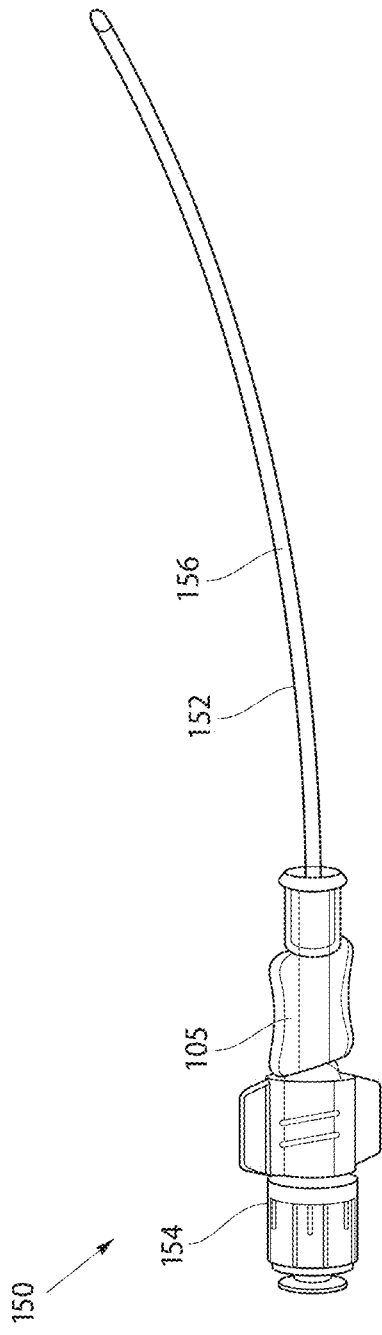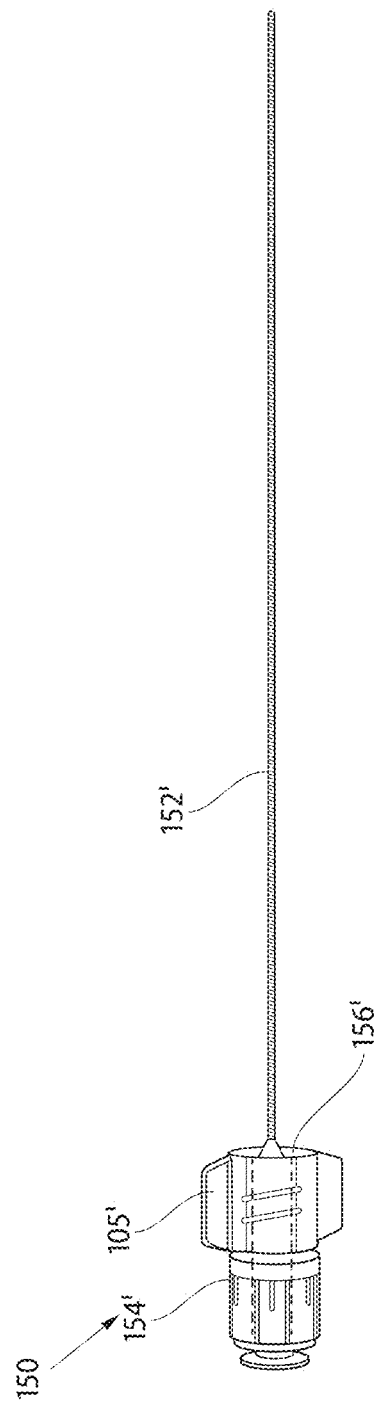
FIG. 2A
FIG. 2B

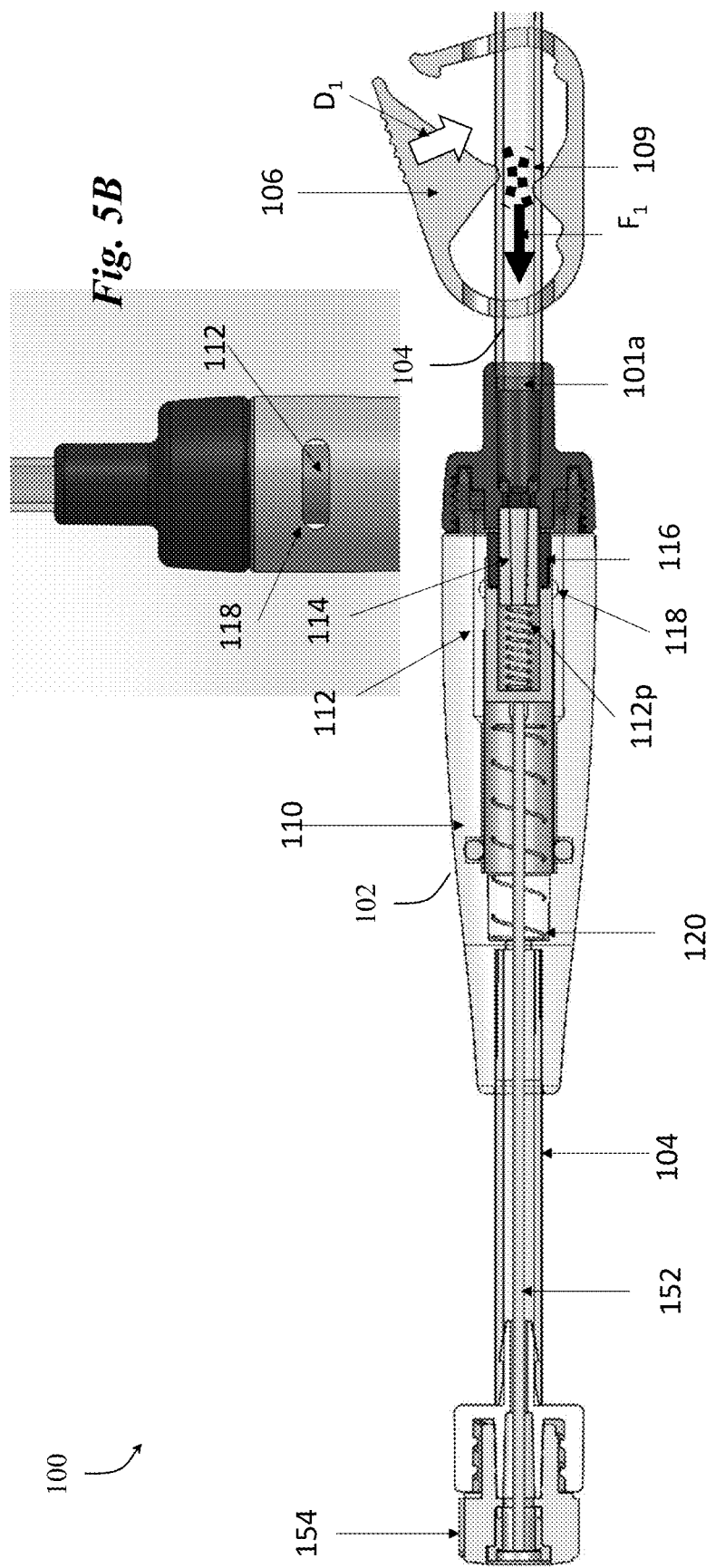

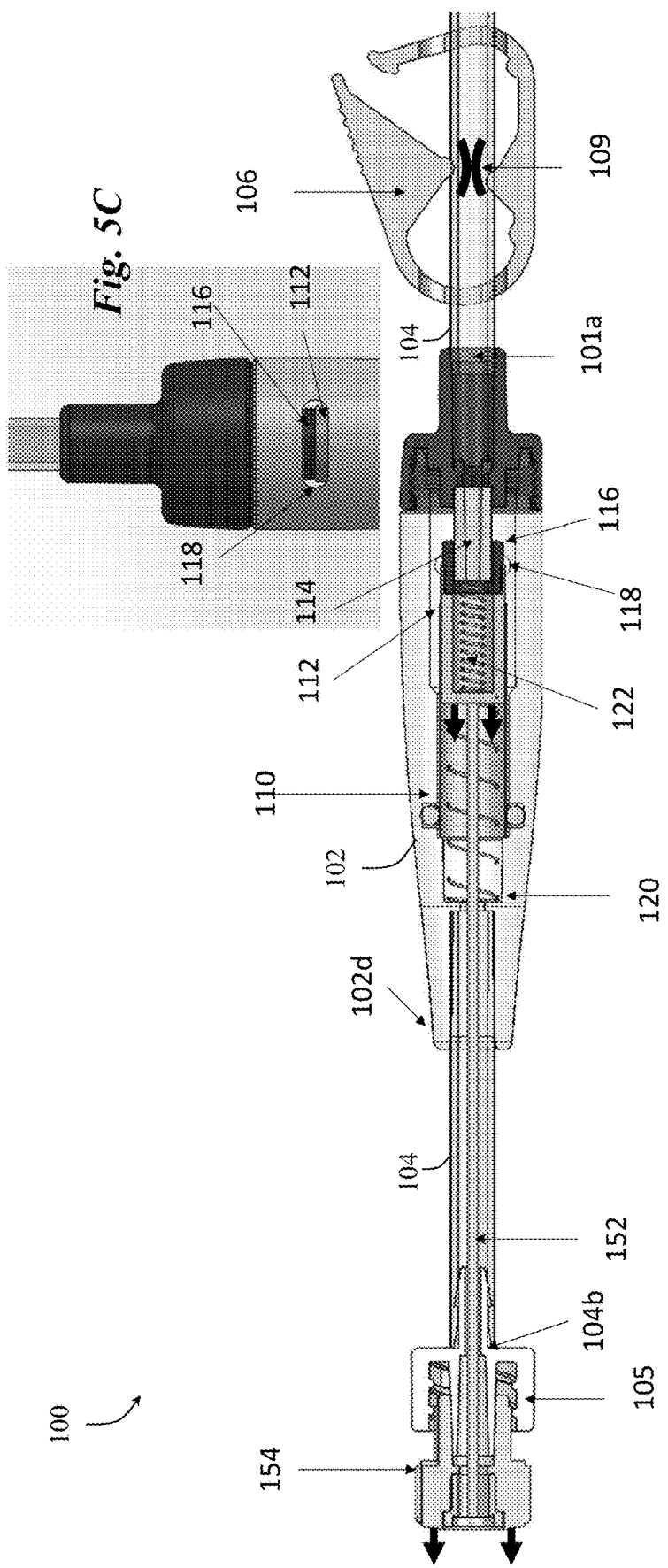

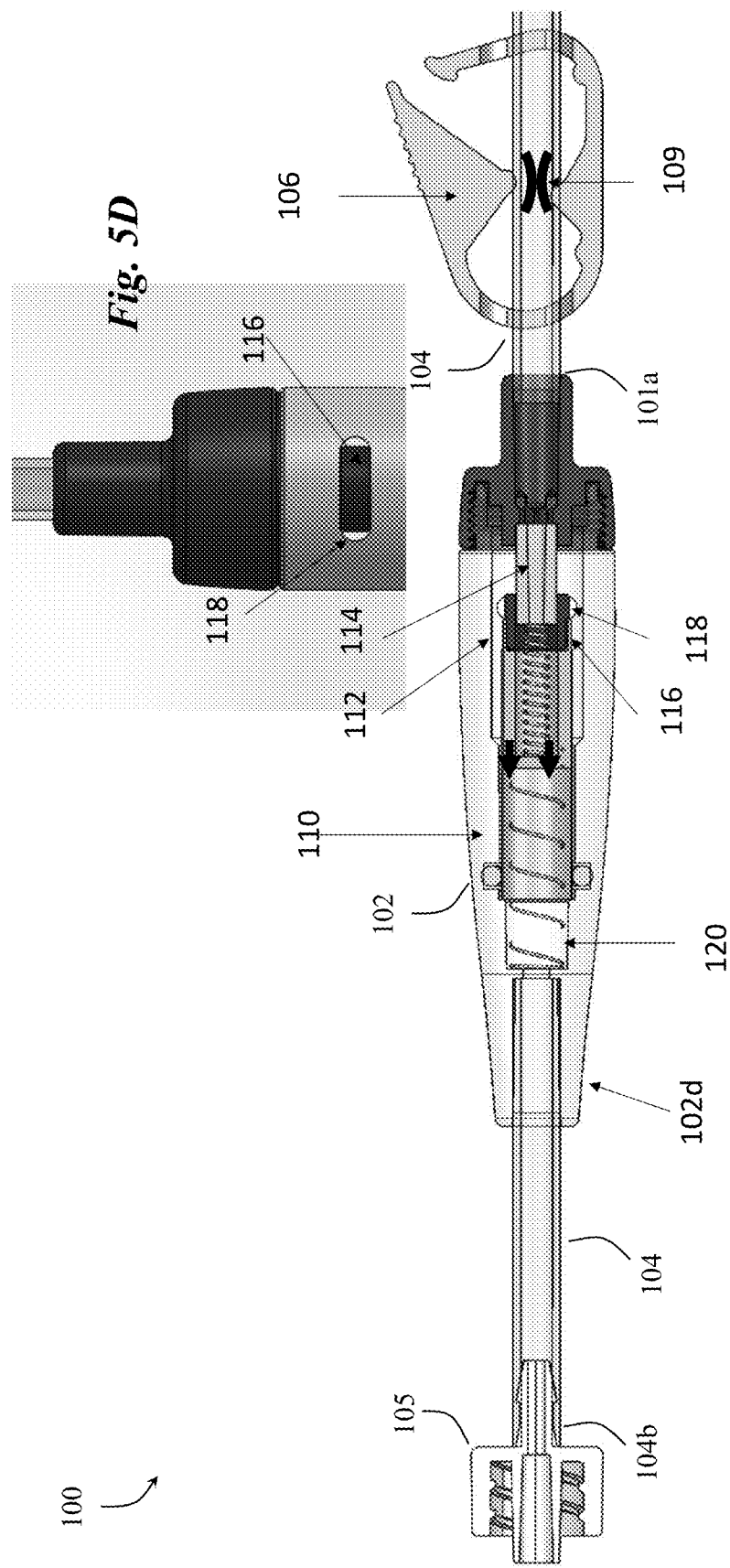

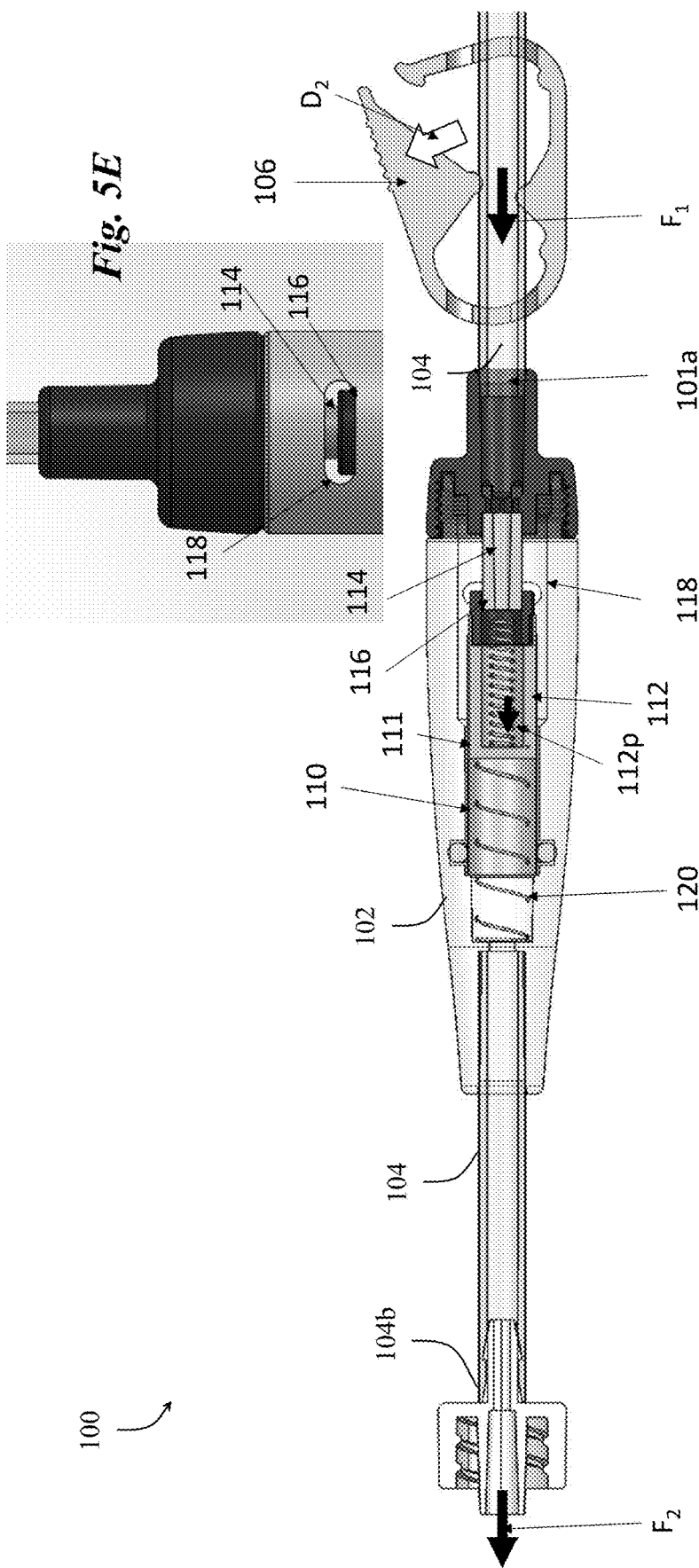

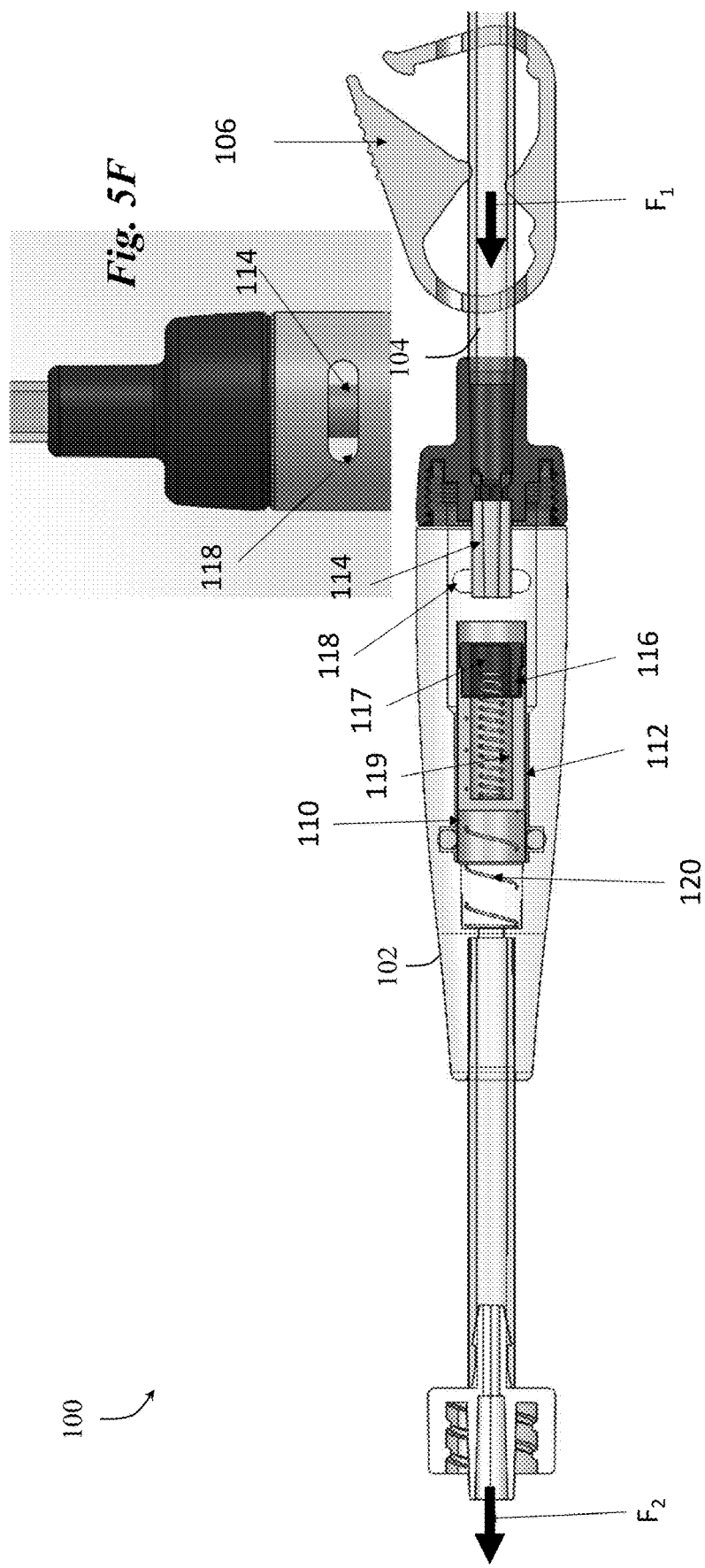

SYSTEMS AND METHODS FOR PRIMING A FLUID LINE

CROSS-REFERENCE TO RELATED APPLICATION

The present application is a 371 U.S. national phase application of International Patent Application No. PCT/US2022/015332, filed Feb. 4, 2022, which claims the benefit of U.S. Provisional Application No. 63/145,824, filed Feb. 4, 2021, the disclosures of which are incorporated herein by reference in their entireties.

FIELD OF THE INVENTION

The present disclosure relates to systems and methods for priming air from a fluid line. In particular, the present disclosure relates to systems and methods that can be used to modify a flow resistor such that air, or other gasses, can be removed from the fluid lines in an efficient manner.

BACKGROUND

Many of fluid transfer applications require that the fluid flow is controlled to deliver a substance to a location at a specified rate. Flow can be controlled by setting the pressure differential, the resistance, or both. These can be actively controlled, but such systems require active pressure sources (e.g., pumps) or resistors (e.g., valves) often with feedback loops based on flow sensors.

Controlling flow completely passively, however, is more difficult. Passive flow resistors (e.g., manual or fixed valves, orifice plates, etc.) are commonly used to control flow but their accuracy are dependent on maintaining a fairly constant pressure. This is typically accomplished with a large reservoir of fluid, (relative to the volume of fluid to be delivered) with stored potential energy that is constant (e.g., elevated tank). A major limitation of this passive variable resistor design is that it is structurally linked to the infusion device and its design is dependent on the device. Perhaps more importantly, its specifications are dependent on the initial conditions, specifically the initial pressure, and the specific trajectory of the pressure for that specific device. The functionality of passive variable resistors would be greatly enhanced and available to a broader set of applications if its design and structure were independent of the pressure source and fluid reservoir and that its resistance was simply a function of the instantaneous pressure difference P at least over a specified range.

One example of a fluid transfer application is patient infusions. Infusions remain ubiquitous in healthcare spanning a wide range of conditions, substances, access sites and venues. Despite advances in oral and other drug delivery modes (e.g., transdermal, inhaled) many critical therapies still require intravenous (IV) infusion. It is estimated that one million infusions are administered per day in the United States. Over 90% of hospitalized patients receive an IV infusion. Infused substances can include drugs (e.g., antibiotics, chemotherapy, pain medications, local anesthetics, vasoactive agents, biologics), fluids (e.g., crystalloids, colloids, parenteral nutrition), and blood products (e.g., red cells, plasma, platelets). These substances are typically infused as (1) a single bolus volume (a few ml to several liters) over a limited time period (e.g., minutes to hours) or (2) a continuous infusion delivered a fixed or titrated rate (typical range 0.1 ml to 5 ml per minute).

Infusions can be administered through a variety of routes, most commonly intravenous but also intraarterial, subcutaneous, intrapleural, intraarticular, epidural, and intrathecal, intraperitoneal, and intramuscular. A wide variety of catheters are available to facilitate infusions in through these various routes. Although traditionally, infusions have been administered in hospital settings, an increasing number of patients are receiving infusions in ambulatory infusion centers and at home. Because these latter settings have fewer, less skilled clinical personnel, only certain infusions are deemed to be safe there such as intravenous antibiotics, certain chemotherapeutic agents, local anesthetics for postoperative pain control, and certain narcotic pain medications.

Healthcare infusions are generally driven by relatively stale technologies such as gravity, active displacement electric pumps, or non-electric disposable elastomeric pumps. All three have well known disadvantages. Gravity driven infusions have low capital and disposable costs but require careful monitoring by a nurse, are not very accurate, limit patient mobility, and have no patient safety features. Electric pumps are accurate (±3%), have built in safety features of debatable efficacy but are expensive, bulky, susceptible to human factors and limit mobility. Additionally, electronic infusion pump errors are a serious ongoing problem and represent a large share of the overall human and economic burden of medical errors. Electronic infusion pumps have become expensive and high maintenance devices, which have been plagued in recent years by recalls due to serious software and hardware problems. These pumps are designed for fine adjustments of infusions in complex patients, such as those in a critical care setting, and their use for routine infusions is technologic overkill. In terms of outpatient infusions, disposable pumps are convenient and fairly inexpensive but have no patient safety features and can be highly inaccurate (±15-40%) and are therefore unsuitable for use with medications where flow accuracy is critical, such as chemotherapeutic. The FDA's MAUDE database includes numerous reports of complications and even deaths resulting from disposable infusion pump flow inaccuracies.

The landmark 1999 Institute of Medicine report, "To Err is Human" (REF), attributed 40-100,000 deaths per year in the U.S. to medical errors. Medication errors, 40% of which are serious, life-threatening, or fatal, are the most common medical error and cost the health care system billions of dollars per year. Intravenous medication errors are the most common medication error and over 35% of these are related to infusion pumps. Studies have shown that despite progressively feature-laden "smart pumps", human factors, software and hardware issue continue to contribute to serious errors (REF). The FDA's MAUDE Adverse Event reporting system contain numerous examples of serious injury and death related to infusion pump errors, both electric and disposable.

In addition to errors related to the infusion flow inaccuracies, gasses, e.g., air, being present in the fluid lines can present severe complications, including death, if those gasses are introduced downstream to a patient or other devices. Currently, when fluid lines have a flow resistor in place, it can take a while for a user to clear air from the lines before the lines can be used for fluid transfer (i.e., five plus minutes). If a procedure is time sensitive, a user may not have time, patience, or the awareness that there is still air present in the lines before continuing with an infusion. Such an error can result in numerous medical complications and in some cases can result in the death of a patient due to the introduction of gas, or air, into the vein of a patient.

Thus, there is a need for improvements for priming air from a fluid line. The present disclosure is directed toward further solutions to address this need, in addition to having other desirable characteristics.

SUMMARY

In accordance with an exemplary embodiment of the present disclosure, a system for exhausting air from within a flow pathway is provided. The system includes a flow resistor having an input designed to be coupled to a fluid source and an outlet designed to output a fluid at an output flow rate; the flow resistor including an adjustable flow channel for modifying the output flow rate of the fluid flowing through the flow resistor. The system further includes a priming device having an elongated portion, the elongated portion being substantially rigid axially and configured for insertion through the outlet of the flow resistor to engage the flow resistor and adjust the output flow rate to allow air to be exhausted from the flow pathway through the flow resistor.

In accordance with aspects of the present disclosure, the outlet of the flow resistor can include a fitting. The priming device can include a cap at an end of the elongated portion, the cap can be configured to couple to the fitting when the elongated portion is disposed in the flow resistor. The priming device can include an open-ended lumen extending throughout the elongated portion, the elongated portion having sufficient axial strength to modify an operation of the flow resistor. The flow resistor can have a piston situated within the flow resistor to define the adjustable flow channel, the piston can be moveable within the flow resistor to adjust the adjustable flow channel; and the output flow rate can be a fixed flow rate. The priming device can be configured to engage the piston within the flow resistor.

The system can further include a viewing window conveying a status of the system to a user. The status of the system can include a priming mode where trapped air can be exhausted through the flow resistor, a flow restriction mode where the output flow rate is modified, and no flow mode where there is no fluid flowing through the flow resistor. The system can further include a clamp for stopping a flow through the flow resistor.

In accordance with exemplary embodiments of the present disclosure, a method for exhausting air from within a flow pathway is provided. The method includes inserting an elongated portion of a priming device through an output end of a flow resistor in fluid communication with the flow pathway, where the flow resistor includes an adjustable flow channel; advancing the elongated portion into the flow resistor to engage the flow resistor and adjust an output flow rate of the flow resistor such that the flow resistor allows for a sufficient clearing flow rate therethrough; and allowing trapped air within the flow pathway to enter the flow resistor and be exhausted from the flow pathway.

In accordance with aspects of the instant disclosure, the method can further include, after the advancing step, engaging a clamp on an inlet tube connected to an input end of the flow resistor to stop fluid flow through the flow resistor. The priming device can be decoupled from the flow resistor, after the clamp is engaged, and the priming device is removed from the flow resistor. A dispensing structure can be coupled to a fitting of the flow pathway to dispense fluid from the flow resistor to a desired destination.

In some embodiments, the method can further include disengaging the clamp on the inlet tube to allow a flow of fluid to enter the flow resistor at an input flow rate. The flow resistor can adjust the input flow rate to a predetermined fixed output flow rate. The flow resistor can passively adjust the input flow rate. The elongated portion can be an open-ended lumen extending throughout the elongated portion, where the elongated portion has sufficient axial strength to modify an operation of the flow resistor.

In accordance with exemplary embodiments of the instant disclosure, a device for de-airing a flow pathway is provided. The device includes a cap portion having an opening, the cap portion configured to removably attach the device to the flow pathway; and an elongated portion extending distally from the cap portion, the elongated portion being substantially rigid axially and being provided with a diameter sufficiently sized to be removably inserted into a flow resistor through an output end of the flow resistor, the elongated portion configured to engage the flow resistor and adjust an output flow rate of the flow resistor to allow air to be exhausted from the flow pathway through the flow resistor.

In some embodiments, the cap portion can be configured to couple to a fitting in fluid communication with a distal end of the flow resistor. The elongated portion can include an open-ended lumen extending throughout the elongated portion and in communication with the opening of the cap portion, where the elongated portion has sufficient column strength to modify an operation of the flow resistor. The elongated portion can be a solid stylet. The elongated portion can be configured to engage a piston across an output end of the flow resistor and to displace the piston to allow the air to be exhausted from the flow pathway.

BRIEF DESCRIPTION OF THE FIGURES

These and other characteristics of the present disclosure will be more fully understood by reference to the following detailed description in conjunction with the attached drawings, in which:

FIGS. 2A and 2B are side views of priming devices, as discussed in accordance with the present disclosure;

FIGS. 4A-4F illustrate an example of operation of the fluid delivery system, as discussed in accordance with the present disclosure; and FIGS. 5A-5F illustrate an example of operation of the fluid delivery system, as discussed in accordance with the present disclosure.

DETAILED DESCRIPTION

Figure 1:
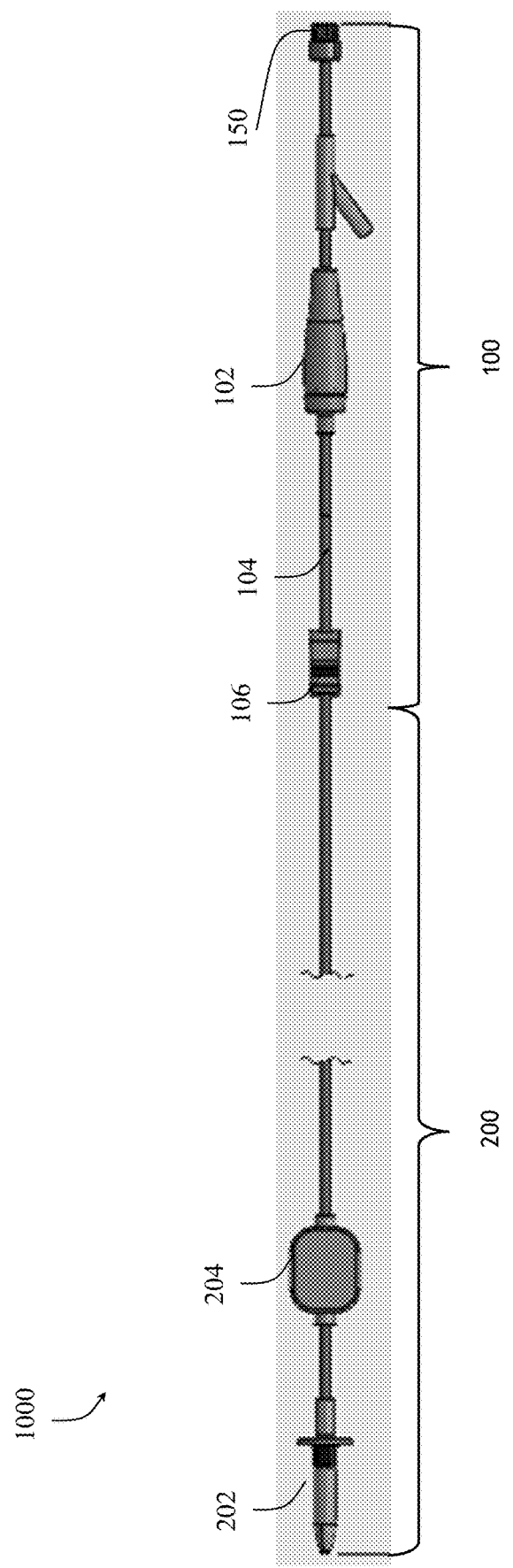
FIG. 1 is a side view of a fluid delivery system, as discussed in accordance with the present disclosure.

An illustrative embodiment of the present disclosure relates to systems and methods suitable for priming air from a fluid line. In particular, the present disclosure relates to systems and methods that can be used to modify a flow resistor such that air can be removed from the fluid lines in an efficient manner.

FIGS. 1 through 5F, wherein like parts are designated by like reference numerals throughout, illustrate an example embodiment or embodiments of improved operation for priming a fluid line, according to the present disclosure.

Although the present disclosure will be described with reference to the example embodiment or embodiments illustrated in the figures, it should be understood that many alternative forms can embody the present disclosure. One of skill in the art will additionally appreciate different ways to alter the parameters of the embodiment(s) disclosed, such as the size, shape, or type of elements or materials, in a manner still in keeping with the spirit and scope of the present disclosure.

Referring to FIG. 1, there is illustrated an assembly 1000 for delivering a fluid from a fluid source (not shown), along a pathway 104, to a site of interest. The assembly 1000 can, in general, include a fluid input component 200 in fluid communication with the fluid source, and a fluid output system ("the system") 100 for directing fluid to the site of interest. Fluid input component 200, in one embodiment, can include any design, structure, or a combination thereof. For example, the fluid input component 200 can include a spike 202 that can be inserted into a fluid source, e.g., an IV bag, and a pump 204, e.g., a disposable pump, to help regulate fluid flow, as the fluid is dispensed from the fluid source through the pathway 104 of assembly 1000. The fluid output system 100, on the other hand, can include any structure, as discussed herein, for clearing air and/or fluid from the pathway 104, as well as regulating the flow rate of the fluid moving therealong. In some embodiments, the system 100 can include a clip 106, a flow resistor 102 designed to modify a flow rate along the pathway 104, and a priming device 150. The clip 106, in one embodiment, can be disposed around an outer surface of the pathway 104 for cutting off or stopping fluid flow along the pathway 104, when activated. Pathway 104, in an embodiment, can be any conduit known in the art capable of accommodating fluid flow from a source to a point of interest, for example, flexible tubing, a catheter, or any structure provided with a lumen.

Downstream of the clip 106 along pathway 104, a flow resistor 102 can be provided. Flow resistor 102, in accordance with one embodiment of the present invention, can be any flow resistors known in the art. For example, the flow resistor 102 can be a passive fixed flow resistor as discussed in U.S. application Ser. No. 16/845,752 or an adjustable flow resistor as discussed in PCT International Application No. PCT/US22/14834, both of which are hereby incorporated herein by reference in their entirety. In certain instances, fluid being introduced into the flow resistor 102 from pathway, or tubing, 104 may include unwanted, trapped, air that needs to be removed from the assembly 1000 prior to delivering to the site of interest, i.e., patient, as the presence of air in fluid can cause complication and present health risks in the patient. To that end, the assembly 1000 can be provided with a priming device 150 to aid in the removal of unwanted air.

Referring now to FIGS. 2A and 2B, examples of various priming devices 150 for removing air from the pathway 104, e.g., in the fluid being introduced into flow resistor 102, are provided. By way of example, the priming devices 150 can be used to remove air or other gases in the pathway 104, entering the flow resistor 102, or within the flow resistor 102. In some embodiments, the priming device 150 can include an elongated portion 152 or 152' and a cap 154, 154' (or cap portion). In the illustrated embodiments of FIGS. 2A and 2B, the cap 154, 154' is shown attached to a fitting 105, 105' which can be used to connect the cap 154, 154' to the pathway 104. The elongated portion 152, 152', in an embodiment, can be designed to fit within an outlet 104b of the pathway 104 (see FIG. 3B) and extend into, at least partially, within a flow resistor 102. In particular, the elongated portion 152, 152' can have an outer diameter that is less than the inner diameter of outlet 104b of the pathway 104 such that the elongated portion 152, 152' can slide at least partially within the flow resistor 102. The elongated portion 152, in an embodiment, can be a hollow tube, as shown in FIG. 2A. The elongated portion 152', in alternative embodiments, can be solid, as shown in FIG. 2B. The elongated portion 152, 152', in certain embodiments, as shown in FIGS. 2A and 2B, is imparted with sufficient radial flexibility to navigate within the pathway 104 to the flow resistor 102 while having sufficient columnal strength (i.e., strength axially or along the central axis) to apply a pushing force within the flow resistor 102 to modify a state of the flow resistor 102, as discussed in greater detail herein. In some embodiments, the elongated portion 152 can be a catheter, as illustrated in FIG. 2A. Alternatively, the elongate portion can be a stylet 152', as seen in FIG. 2B. The stylet 152', similar to the catheter, can be provided with sufficient axial strength and sufficient radial flexibility. In an embodiment, the elongated portion 152, 152' can be a rigid yet malleable component sized to fit inside the pathway 104 while allowing for conformity to the pathway's 104 shape. Alternatively, other elongate structures can be used in place of the catheter 152 or the stylet 152' so long as they are provided with axial strength and radial flexibility.

Figure 3A:
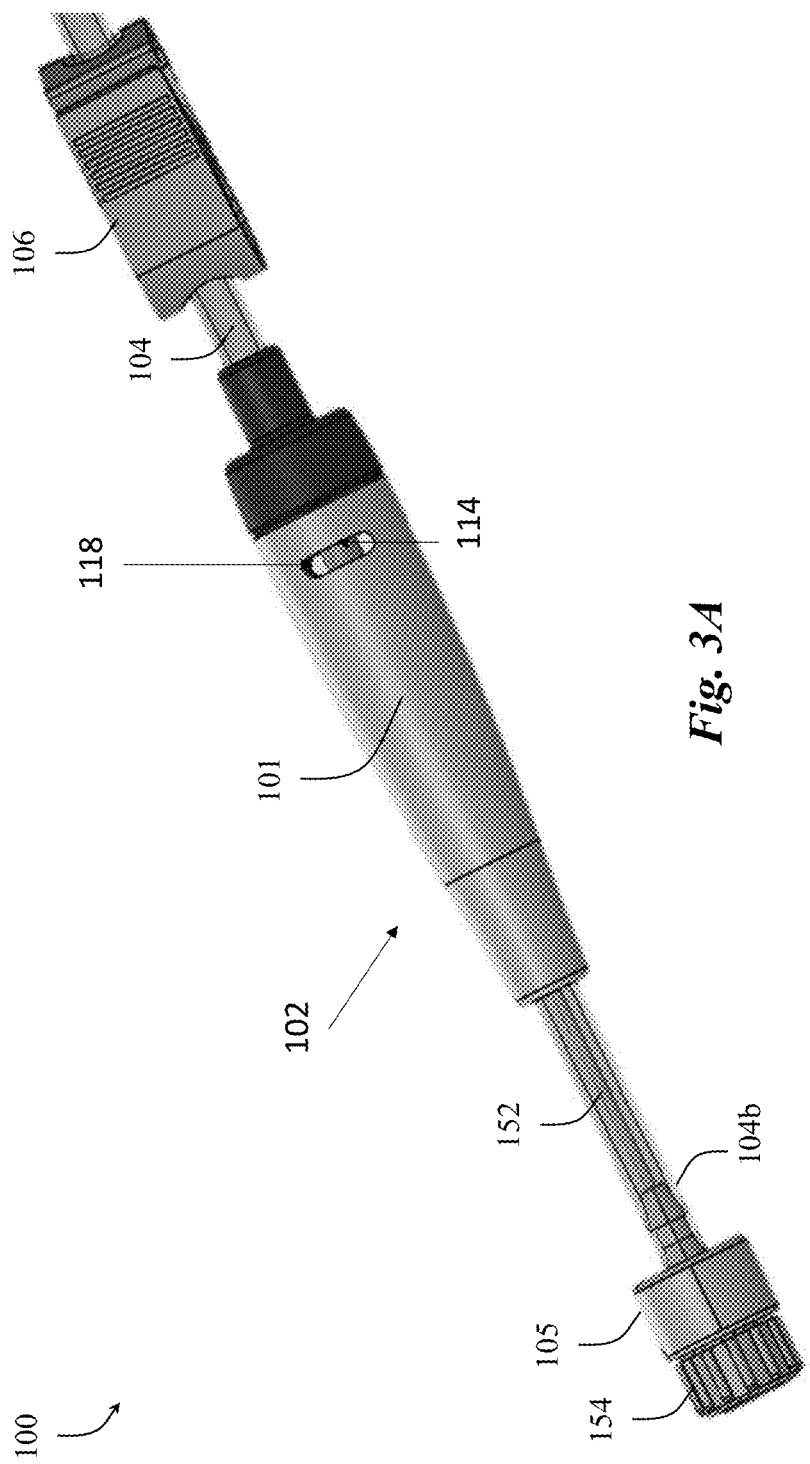
FIG. 3A is a perspective view of a fluid delivery system, as discussed in accordance with the present disclosure.
Figure 3B:
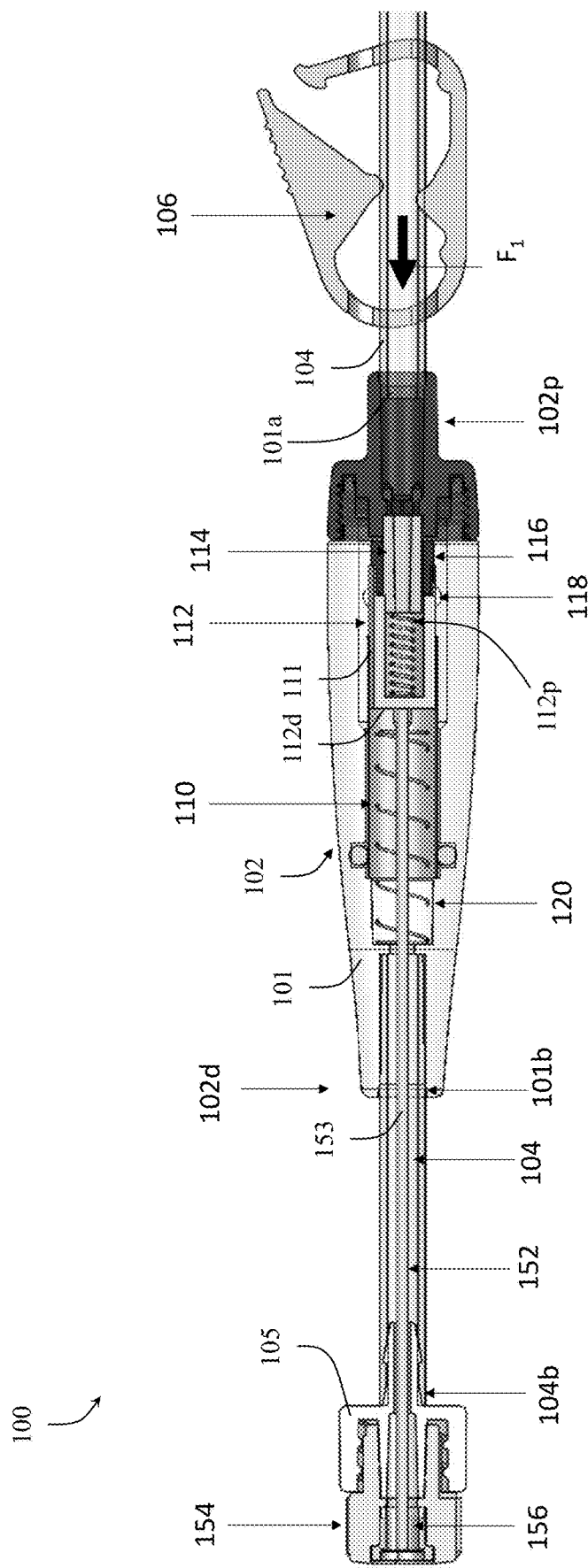
FIG. 3B is a cross-sectional side view of a fluid delivery system, as discussed in accordance with the present disclosure.
Figure 3C:
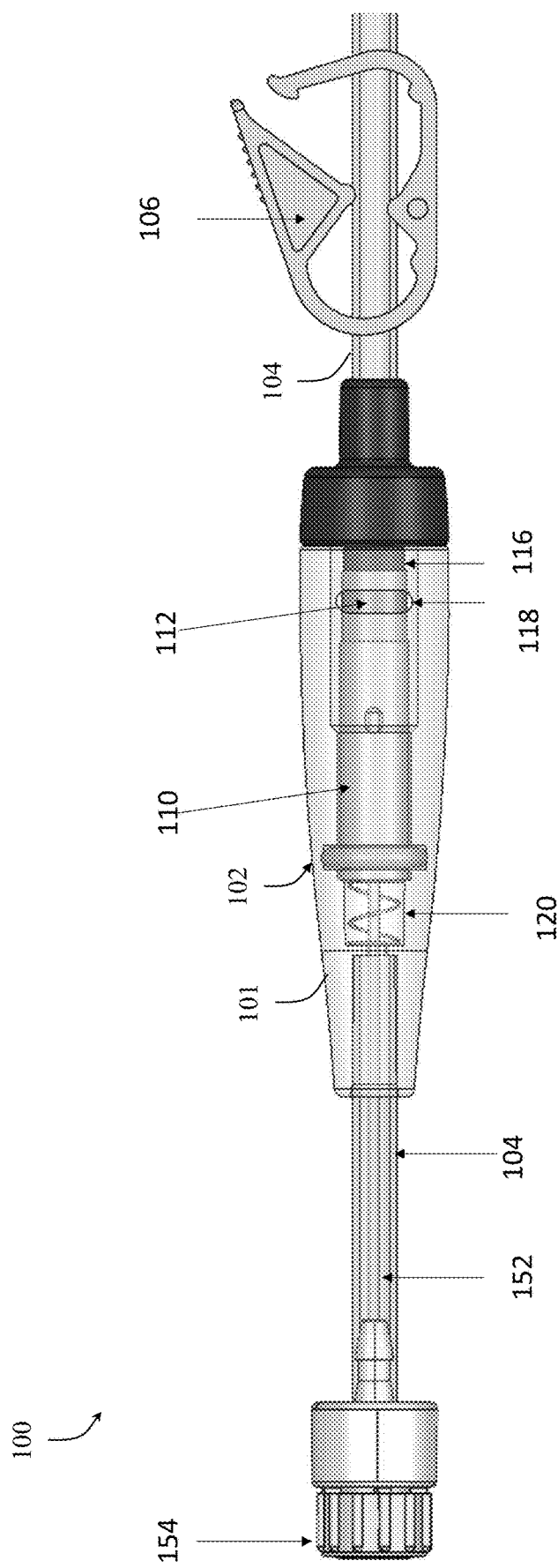
FIG. 3C is a side view of a fluid delivery system, as discussed in accordance with the present disclosure.

The cap 154 of priming device 150, as illustrated in FIGS. 3A-3C, can include, in one embodiment, an open channel 156 such that, when in combination with the elongated portion 152, it creates a lumen 153, or an open-ended channel, running through the elongated portion 152 to the cap 154 along the entire length of the priming device 150. In another embodiment, the cap 154' of priming device 150' can include an open channel 156' such that, when coupled to the fitting 105' and pathway 104, the open channel 156' creates an open-ended channel running the entire length of the priming device 150' to allow for air and fluid to flow between the outer surface of the stylet 152' and inner surface of the pathway 104 and exit through the cap 154'. The cap 154, 154' can include any combination of mechanisms that enable it to be removably coupled the fitting 105, 105', to the pathway 104, or other parts of the assembly 1000. For example, the cap 154 can be a connecter that can couple to a Luer fitting, or fixture, 105 positioned on a distal end 102d of the flow resistor 102. In some embodiments, the priming device 150 can be combined with the flow resistor 102, as shown in FIGS. 3A-4F, to provide the priming of the system 100.

In some embodiments, the flow resistor 102 can generally include a housing 101 containing a cylinder 110 (or flow chamber/channel/cross-sectional area) and a piston 112 (or a flow modifier) disposed within the housing 101. The housing 101 can include an inlet 101a and an outlet 101b. The piston 112 can be movably disposed within the cylinder, depending on the mode of operation, to create a flow channel 111 to control a flow rate of a fluid passing therethrough. The piston 112, in an embodiment, can have a proximal end 112p and a distal end 112d. The distal end 112d of the piston 112 can be coupled to a spring 120 to resist movement of the piston 112, as constrained within the cylinder 110, in the distal direction in response to an input flow $F_1$. For example, a fluid can have an input flow $F_1$ through the flow resistor 102 from the pathway 104, through a flow channel 111 arranged between the cylinder 110 and the piston 112. The input flow $F_1$, as seen in FIG. 3B, can apply a pressure against the proximal end 112p of the piston 112. The balance of pressures, or forces, applied to the proximal end 112p and the distal end 112d, of the piston 112, can create a flow channel 111, having a predefined length, through the cylinder 110 to modify the flow rate of the input flow $F_1$. Specifically, by directing the input flow $F_1$ through the flow channel 111, the flow can be slowed to a desired fixed rate, due to the laminar flow of the fluid through a relatively narrow flow channel 111. The ability of the flow resistor 102 to affect the input flow $F_1$ can, alternatively, be obtained using any combination of flow resistors known in the art. For example, the flow resistor 102 can be a flow resistor as discussed in U.S. application Ser. No. 16/845,752 or PCT International Application No. PCT/US22/14834, both incorporated herein by reference in their entirety.

In addition to the cylinder 110 and the piston 112, the flow resistor 102 can include a first visual indicator 114, a second visual indicator 116, and a viewing window 118. For example, a combination of the piston 112, the first visual indicator 114, the second visual indicator 116, and the viewing window 118 can provide visual cues to a user for the priming state and/or operating state of the flow resistor 102. As seen in FIG. 3C, the viewing window 118 can be an opening or a transparent portion of the housing 101 to permit the piston 112, the first visual indicator 114, and the second visual indicator 116 to be seen, so as to provide a visual status of the system 100. In some embodiments, each of the piston 112, the first visual indicator 114, and the second visual indicator 116 can be seen through the viewing window 118 in respective various modes of operation for the flow resistor 102. For example, the piston 112 can be seen in the viewing window 118 when the system 100 is in priming mode, while the first visual indicator 114 can be seen in the viewing window 118 when there is sufficient input flow $F_1$ through the flow resistor 102 to displace the piston 112, and the second visual indicator 116 can be seen in the viewing window 118 when there is no flow entering the inlet 101a of the flow resistor 102 (e.g., when a clip 106 is pinching the pathway 104 leading into the flow resistor 102). The configurations for the system 100 for each of the visualizations, and partial visualizations, are discussed in greater detail with respect to FIGS. 4A-5F. While the foregoing discussion explains the function of the priming mode and the viewing window 118 in combination, it will be appreciated that the flow resistor 102 can include just the priming mode features or just the viewing window functionality. For example, the viewing window functionality can be useful to indicate to a user if a flow is passing through the flow resistor or if the flow has come to a stop, without consideration for a priming mode.

Still referring to FIGS. 3A-3C, system 100 with the priming device 150 being inserted into the outlet 104b of the pathway 104 is depicted. As shown in FIG. 3A, the elongated portion 152 of the priming device 150 can be inserted through the outlet 104b of the pathway 104 and into at least a portion of the flow resistor 102. In some embodiments, the cap 154 can be secured, for example, by screw threads, onto a fitting 105 (e.g., a Luer fitting) arranged at the outlet 104b of the pathway 104. It should be noted that other means for securing the cap 154 onto the fitting 105 can be employed without deviation from the disclosure of the present invention. The fitting 105, in an embodiment, can be placed substantially in line with the pathway 104. In some embodiments, when the priming device 150 is secured onto the fitting 105, the elongated portion 152 has a sufficient length to extend into the flow resistor 102, to contact distal end 112d of the piston 112, and to displace the piston 112 toward proximal end 102p of the flow resistor 102. The displacement of the piston 112 can be sufficient to maximize an amount of flow that will pass through the flow resistor 102. When the piston 112 is displaced towards the proximal end 102p, by the elongated portion 152, a flow channel 111 disposed between the piston 112 and the cylinder 110 can be opened such that the input flow $F_1$ is not slowed, or minimally slowed, by any laminar flow. The fluid can then enter the lumen 153 within the catheter to exit through the cap 154. When the flow channel 111 is opened by the elongated portion 152, a fluid can flow through the flow resistor 102 at a sufficient flow rate to clear out any air that may be in the pathway 104, or the flow resistor 102, in an efficient and quick manner. This clearing flow rate, or priming mode, can be visualized by the piston 112 being advanced over, or otherwise displacing, the first visual indicator 114 and/or the second visual indicator 116 such that piston 112 itself is viewable through the viewing window 118, as seen in FIG. 3C. It should be appreciated that although reference is made to elongated portion 152 in connection with priming device 150, similar operation can be accomplished with stylet 152' in connection with priming device 150.

Figure 5A:
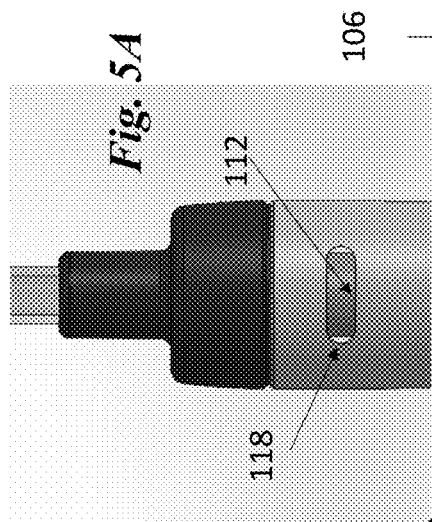
Figure 4A:
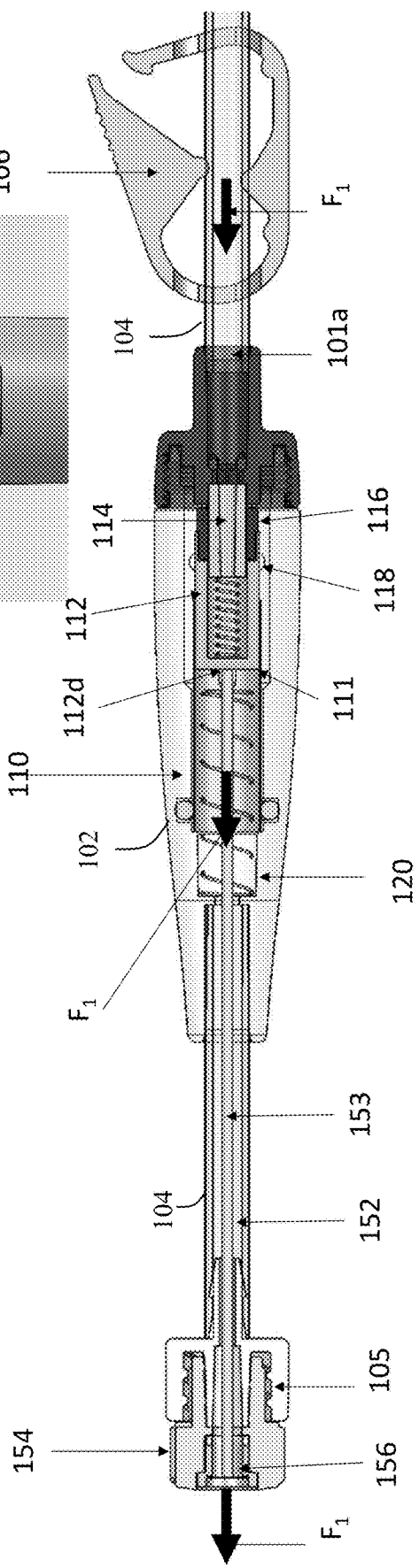

Referring to, FIGS. 4A-4F, a detailed example operation of the system 100 through the priming mode is depicted. FIG. 4A depicts an initial, or priming mode, of the system 100 when the priming device 150 is inserted within the pathway 104, as discussed with respect to FIGS. 3A-3C. As illustrated in FIG. 4A, in the priming mode, the elongated portion 152 can be inserted through the outlet 104b of the pathway 104 and into the flow resistor 102 to displace the piston 112 as the cap 154 of the priming device 150 is attached to the fitting 105. The elongated portion 152 can, for example, engage the distal end 112d of the piston 112 to push the piston in a proximal direction towards the inlet 101a. In some embodiments, during the priming mode shown in FIG. 4A, the clip 106 is not activated, such that the clip 106 is not pinching the pathway 104, allowing uninterrupted input flow $F_1$ through the pathway 104 into the inlet 101a of the flow resistor 102. As an input flow $F_1$ enters into the inlet 101a, while the piston 112 in the proximal most position within the flow resistor 102, the fluid flowing through the flow resistor 102 will have a maximized and/or substantially unmodified flow rate. The flow rate through the flow resistor 102 in the priming mode can be substantially unmodified from the input flow $F_1$ because when the piston 112 is displaced proximally by the elongated portion 152, the piston 112 may not be within the cylinder 110 such that there is a minimal, or no, flow channel 111 created between the piston 112 and the cylinder 110. As the input flow $F_1$ does not pass through a flow channel 111, the flow of a liquid is not slowed by the flow resistor 102 in the priming mode as it exits through the lumen 153 of the elongated portion 152. This unmodified flow rate can allow for the system 100 to exhaust air, or other gasses, from within any location in the assembly 1000 (e.g., de-air, or exhaust, the system) at an expedited rate. In some embodiments, the priming mode can be visualized to a user via the viewing window 118 showing the piston 112, as shown in FIG. 5A. This visualization can be achieved by the piston 112 being advanced proximally within the flow resistor 102 such that it is axially aligned with the viewing window 118, during the priming mode.

Once the system 100 has been de-aired, as shown in FIG. 4A, the system 100 can be transitioned to a first transition state of the system 100 when the system 100 is ready to be setup for use to dispense the fluid to an intended destination. In the first transition state as shown in FIG. 4B, for example, a clip 106 that is disposed proximally, or upstream, of the inlet 101a can be activated. The clip 106 can be pushed in a first direction D1 to pinch, or constrict, the pathway 104 closed, shown as pinch 109 in phantom, such that there is no additional flow of fluid into the flow resistor 102. Where other clips are used in alternative embodiments, those clips may not "pinch," or clamp the pathway 104, but will restrict the flow through the tubing via other means. When the input flow F1 has been stopped from flowing into the inlet 101a, the fluid does not apply a pressure on the proximal end 112p of the piston 112. In the illustrated embodiment, when the clip 106 is activated after the initial state, there should be no change to the other components within the system 100. This means that visualization of the piston 112 in the viewing window 118 will remain unchanged, as shown in FIG. 5B, because the elongated portion 152 is still maintaining the piston 112 in the proximal most position within the flow resistor 102. With the clip 106 pinching the pathway 104, there will be no additional fluid flow into the flow resistor 102 and this will allow a user to remove the priming device 150 for use of the system 100 for fluid delivery.

FIG. 4C depicts a second transition state of the system 100 when the priming device 150 can be removed from the system 100. When in the second transition state, the clip 106 can remain activated to pinch the pathway 104, shown as pinch 109, to stop any additional input flow $F_1$ from passing into the inlet 101a of flow resistor 102. Once the clip 106 stops the flow, the priming device 150 can be removed from the pathway 104 because at this time, all, or substantially all, of the air has been removed from the assembly 1000. In some embodiments, removing the priming device 150 can include unsecuring the cap 154 from the fitting 105 and pulling the cap 154 distally to pull the elongated portion 152 out of the flow resistor 102 and the pathway 104 through the outlet 104b. In other embodiments, the cap 154 may not be threaded onto the fitting 105 and the cap 154 can be pulled without any release from the fitting 105. By removing the elongated portion 152, the piston 112 can begin to transition back to a resting position within flow resistor 102. In some embodiments, a return spring 122 can be disposed between the piston 112 and the first visual indicator 114 to push the piston towards the distal end 102d of the flow resistor 102. Of note, because the clip 106 can still be closed in this state, no flow will pass through the flow resistor 102 due to the creation of a vacuum within the flow resistor 102 preventing any additional fluid from exiting the system 100. The lack of additional flow exiting the outlet 104b of the pathway 104 will ensure that the assembly 1000 does not re-fill with air. Removal of the priming device 150 from the pathway 104 can begin to cause the return of the piston 112 to its proper resting position which can be visualized to a user via viewing window 118, as seen in FIG. 5C. In this second transition state, the viewing window 118 can partially show the piston 112 and partially show the second visual indicator 116, as shown in FIG. 5C.

FIG. 4D depicts the system 100 when the priming device 150 has been removed and the assembly 1000 has come to rest. With the priming device 150 removed and the flow resistor 102 properly de-aired, a user can connect the outlet 104b of the pathway 104 to a destination. For example, fitting 105 can remain in the outlet 104b and can be coupled to an IV needle (not shown) for fluid delivery, with additional tubing. In some embodiments, the clip 106 can remain activated to pinch 109 the pathway 104 and stop any additional flow into the flow resistor 102 so that the outlet 104b can be coupled, via the fitting 105, to an output (e.g., IV needle) without the fluid escaping the system 100. For example, with the clip 106 in place, there will be no input pressure/fluid flow acting on the piston 112. Thus, the piston 112 can remain at rest distal to where it is located during the priming mode but proximal to where it is located during normal operation such that the second indicator 116 is axially aligned with the viewing window 118. Therefore, the system 100 can signal to the user that the priming device has been properly removed and there can be a lack of input flow $F_1$ from the pathway 104 into the flow resistor 102 inlet 101a (due to pinched clip 106). The system 100 can visualize this rest state to a user via viewing window 118 showing the fully exposed second visual indicator 116, as shown in FIG. 5D. In some embodiments, only the second indicator 116 can be seen in the window in the rest, or no flow, state. Once the user has confirmed, visually, that the flow resistor 102 is at rest with no flow, the user can attach the flow resistor 102 to the destination device.

Once the system 100 has been connected to the destination, the system 100 can be transitioned to a second transition state, as seen in FIG. 4E, where the clip 106 is deactivated and an input fluid flow $F_1$ is allowed to enter the inlet 101a of the flow resistor 102. As shown in FIG. 4E, the clip 106 is opened by moving it in a second direction $D_2$ such that the pathway 104 is opened and is no longer pinched 109. In the second transition state, as the input flow $F_1$ enters the inlet 101a of the flow resistor 102, the fluid can apply a distal pressure on a proximal end 112p of the piston 112 to advance the piston 112 from a resting position, as seen in FIG. 4D, distally to a flow regulation position, as shown in FIG. 4E. As the piston 112 is advanced to the flow regulation position, a flow channel 111 can be created between the piston 112 and the cylinder 110. A length of the flow channel 111 can be defined as a function of the pressure differential between the input flow $F_1$ and a backflow pressure from the outlet 104b, e.g., a veinous pressure, as balanced by the spring 120. When the flow channel is, relatively, shorter e.g., at the start of the flow, due to a lower pressure differential, the flow channel 111 can slow the input flow $F_1$ to a desired, or predetermined, fixed rate output flow $F_2$. As the input flow $F_1$ begins to increase, the flow channel can be relatively longer due to a higher pressure differential. Thus, the flow channel 111 can slow the input flow $F_1$ to a larger degree to ensure that the flow rate can remain at the desired fixed output flow rate $F_2$. Again, it should be appreciated that although reference is made to the elongated portion 152, or a catheter, in connection with priming device 150, similar operation can be accomplished with stylet 152' in connection with priming device 150.

In some embodiments, when the system 100 is being transitioned between states, the flow resistor 102 can visualize the transition via the viewing window 118. For example, the viewing window 118 can partially show the second visual indicator 116 and partially show the first visual indicator 114, as shown in FIG. 5E. Additionally, the user can be notified of the transition because an output flow $F_2$ can begin to flow out of the outlet 104b.

Once the input flow $F_1$ has begun to flow at a given input rate, the system 100 can begin a constant flow rate delivery state, as shown in FIG. 4F. When the input flow $F_1$ enters the inlet 101a of the flow resistor 102, the flow channel 111 can passively adjust the input flow $F_1$ without restriction (e.g., by the priming device 150 or clip 106). The constant flow rate delivery state of FIG. 4F can be visualized to a user as the first visual indicator 114 can be the only structure visible through the window 118, as shown in FIG. 5F. When in the constant flow rate delivery state, the piston 112 will adjust within the cylinder 110 to provide a consistent rate of flow being output from the flow resistor, as discussed above. In this constant flow rate delivery state, the flow resistor 102 will act in its normal operation, for example, as discussed in U.S. application Ser. No. 16/845,752 and PCT International Application No. PCT/US22/14834, both incorporated herein by reference in their entirety.

Referring back to FIGS. 5A-5F, as discussed with respect to FIGS. 4A-4F, example indicators for operation of the system 100 are illustrated. The combination of visual indicators can include any combination of mechanisms. In some embodiments, as illustrated, the first visual indicator 114 is fixed at a proximal most location within the flow resistor 102 such that it is axially aligned within viewing of the viewing window 118. The second visual indicator 116 and the piston 112 can be fixed to one another, end to end, such that movement of the piston affects the position of the second visual indicator 116 through the flow resistor 102. Further, the second visual indicator 116 can have a generally cylindrical shaped with a through hole 117, called out in FIG. 4F, sized to telescopically receive the first visual indicator 114 as the second visual indicator 116 is advanced proximally, e.g., during the priming mode of FIG. 4A. Additionally, the piston 112 can similarly have a lumen 119, called out in FIG. 4F, which can extend to, but not through, a distal end 112d of the piston 112. The lumen 119 of the piston 112 can additionally receive a portion of the first visual indicator 114 as the piston 112 is advanced proximally, e.g., during the priming mode of FIG. 4A. As the piston 112 and the second visual indicator 116 can receive a portion of the first visual indicator 114; the piston 112 and/or the second visual indicator 116 will be viewable within the viewing window 118 as a function of the piston 112 location. In some embodiments, the body of the flow resistor 102 can be opaque and the viewing window 118 can be clear to allow a clear conveyance of the operation state of the system 100 to a user.

In use, the assembly 1000 of the present disclosure can be used to de-air a pathway 104 to be used for fluid delivery to a destination. For example, the assembly 1000 of the present disclosure can be used to de-air a pathway to be used for fluid delivery in an IV setup. However, the instant disclosure has applicability beyond fluid delivery in an IV setup, for example the assembly 1000 can be used to deliver a fluid, e.g., water, to be mixed with a granulated substance, e.g., concrete mix, where the flow rate of the fluid may be essential to ensure a smooth mix. Additionally, any use case where a de-aired pathway is needed to deliver a fluid at a fixed rate is considered to be within the scope of this disclosure. As would be appreciated by one skilled in the art, the system 100 of the present disclosure can be used with any combination of applications, for example, the system 100 can be used to de-air a brake line, fuel line, water line, etc.

In one example embodiment in a medical fluid infusion setting, an IV pathway can require air to be removed from the assembly 1000, prior to delivering the fluid to a patient (e.g., via the IV needle). Therefore, the pathway 104 may need to be de-aired before delivering a fluid to the patient. However, when a flow resistor, e.g., flow resistor 102, are present, it can take a long-time resistor (e.g., five plus minutes or more) to get air out the assembly 1000 because the flow resistor 102 can create a restricted flow rate. Thus, the instant disclosure provides for a priming device 150 to efficiently de-airing the pathway as discussed above.

Using the system 100 of the present disclosure, a priming device 150 can be used to temporarily modify the resistive functionality of the flow resistor 102 to a substantially free flowing configuration to efficiently de-air the pathway. For example, the elongated portion 152 of the priming device 150 can be inserted into the outlet 104b of the pathway 104 and at least partially into the flow resistor 102. As the elongated portion 152 enters into the flow resistor 102, the elongated portion 152 can advance the piston 112 proximally to create an open flow through the flow resistor 102 without the piston 112 creating restricted flow channel 111, as it would in normal operation. The elongated portion 152 can be sufficiently flexible to navigate the flow resistor 102 while maintaining sufficient column strength to displace piston 112, thereby canceling the flow restriction when de-airing the system 100. To secure the elongated portion 152 in place against the piston 112 for de-airing, the priming device 150 can include a cap 154 which can be coupled to the fitting 105 at the outlet 104b of the pathway 104 (e.g., with a Luer fitting). With the priming device 150 in place against the piston 112, the priming device 150 can create an open pathway (or channel) running through the pathway 104 through the elongated portion 152 and out the cap 154.

After de-airing the flow pathway, a clip 106, disposed upstream of the flow resistor 102, can be activated to pinch off the pathway 104 to stop fluid from flowing into the flow resistor 102. Once the flow of fluid into the flow resistor 102 has been stopped, the priming device 150 can be removed from the flow resistor 102. For example, the cap 154 can be decoupled from the fitting 105 (e.g., via a Luer fitting) and the elongated portion 152 can be pulled out of the flow resistor 102. With the priming device 150 removed from the system 100, the delivery mechanism (e.g., an IV needle) can be coupled to the fitting 105 of the pathway 104. Lastly, the clip 106 can be released from pinching the pathway 104 upstream from the flow resistor 102. As fluid flows into the flow resistor 102, the flow resistor 102 can operate as normal to restrict the flow rate to a desired constant flow rate $F_2$. The flow resistor 102 can, in some embodiments, include a viewing window 118 which can show the various states of the system 100 throughout the de-airing and operating states.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present disclosure will be apparent to those skilled in the art in view of the foregoing description. Accordingly, this description is to be construed as illustrative only and is for the purpose of teaching those skilled in the art the best mode for carrying out the present disclosure. Details of the structure may vary substantially without departing from the spirit of the present disclosure, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present disclosure be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A system for exhausting air from within a flow pathway, the system comprising:
   a flow resistor having an input designed to be coupled to a fluid source and an outlet designed to output a fluid at an output flow rate;
   the flow resistor comprising a cylinder and a piston, the piston movably disposed within the cylinder, an adjustable flow channel for modifying the output flow rate of the fluid flowing through the flow resistor, a first visual indicator, and a second visual indicator; and
   a priming device having an elongated portion, the elongated portion being substantially rigid axially and configured for insertion through the outlet of the flow resistor to engage the piston of the flow resistor such that the piston is disposed proximally towards the input and relative to the cylinder to adjust the output flow rate to allow air to be exhausted from the flow pathway through the flow resistor;
   wherein the priming device further includes a viewing window conveying a status of the system to a user, wherein the status of the system includes at least a priming mode where trapped air can be exhausted through the flow resistor and wherein during this priming mode, the piston is displaced such that the first and the second visual indicators are not viewable within the viewing window.

2. The system of claim 1, wherein the outlet of the flow resistor includes a fitting.

3. The system of claim 2, wherein the priming device includes a cap at an end of the elongated portion, the cap configured to couple to the fitting when the elongated portion is disposed in the flow resistor.

4. The system of claim 1, wherein the priming device comprises an open-ended lumen extending throughout the elongated portion, the elongated portion having sufficient axial strength to modify an operation of the flow resistor.

5. The system of claim 1, wherein:
   the piston situated within the flow resistor to define the adjustable flow channel, the piston being moveable within the flow resistor to adjust the adjustable flow channel; and
   the output flow rate is a fixed flow rate.

6. The system of claim 5, wherein the priming device is configured to engage the piston within the flow resistor.

7. The system of claim 1, further comprising a clamp for stopping a flow through the flow resistor.

8. The device of claim 1, wherein the status of the system further includes a flow restriction mode where the output flow rate is modified, and no flow mode where there is no fluid flowing through the flow resistor, wherein in the flow restriction mode, the first visual indicator is viewable through the viewing window and in the no flow mode the second visual indicator is viewable through the viewing window.

9. A method for exhausting air from within a flow pathway, the method comprising:
   inserting an elongated portion of a priming device through an output end of a flow resistor in fluid communication with the flow pathway, the flow resistor comprising a cylinder, a piston, an adjustable flow channel, a first visual indicator and a second visual indicator;
   advancing the elongated portion into the flow resistor to directly engage the piston of the flow resistor to be arranged proximally relative towards an input of the flow resistor and adjust an output flow rate of the flow resistor such that the flow resistor allows for a sufficient clearing flow rate therethrough; and
   allowing trapped air within the flow pathway to enter the flow resistor and be exhausted from the flow pathway;
   wherein the priming device includes a viewing window such that advancing the elongated portion causes the piston to be visible in the viewing window and causes the first visual indicator and the second visual indicator to not be visible through the viewing window.

10. The method of claim 9, wherein after the advancing step, engaging a clamp on an inlet tube connected to an input end of the flow resistor to stop fluid flow through the flow resistor.

11. The method of claim 10, wherein the priming device is decoupled from the flow resistor, after the clamp is engaged, and the priming device is removed from the flow resistor.

12. The method of claim 11, wherein a dispensing structure is coupled to a fitting of the flow pathway to dispense fluid from the flow resistor to a desired destination.

13. The method of claim 11, further comprising disengaging the clamp on the inlet tube to allow a flow of fluid to enter the flow resistor at an input flow rate.

14. The method of claim 13, wherein the flow resistor adjusts the input flow rate to a predetermined fixed output flow rate.

15. The method of claim 9, wherein the elongated portion comprises an open-ended lumen extending throughout the elongated portion, the elongated portion having sufficient axial strength to modify an operation of the flow resistor.

16. A device for de-airing a flow pathway, the device comprising: a cap portion having an opening, the cap portion configured to removably attach the device to the flow pathway; and an elongated portion extending distally from the cap portion, the elongated portion being substantially rigid axially and being provided with a diameter sufficiently sized to be removably inserted into a flow resistor through an output end of the flow resistor, the elongated portion configured to engage a piston of the flow resistor such that the piston is displaced proximally towards an input of the flow resistor to adjust an output flow rate of the flow resistor to allow air to be exhausted from the flow pathway through the flow resistor, the flow pathway extending entirely externally to the piston.

17. The device of claim 16, wherein the cap portion is designed to couple to a fitting in fluid communication with a distal end of the flow resistor.

18. The device of claim 16,
wherein the elongated portion comprises an open-ended lumen extending throughout the elongated portion and in communication with the opening of the cap portion, and
wherein the elongated portion has sufficient column strength to modify an operation of the flow resistor.

19. The device of claim 16, wherein the elongated portion is configured to engage the piston across an output end of the flow resistor and to displace the piston to allow the air to be exhausted from the flow pathway.

\* \* \* \* \*